(12) United States Patent
Kurita et al.

(10) Patent No.: US 8,727,984 B2
(45) Date of Patent: May 20, 2014

(54) ULTRASOUND DIAGNOSIS APPARATUS

(75) Inventors: Koichiro Kurita, Tochigi-ken (JP); Osamu Nakajima, Tochigi-ken (JP); Masaru Ogasawara, Tochigi-ken (JP); Satoshi Matsunaga, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1251 days.

(21) Appl. No.: 12/580,811

(22) Filed: Oct. 16, 2009

(65) Prior Publication Data

US 2010/0099988 A1  Apr. 22, 2010

(30) Foreign Application Priority Data

Oct. 16, 2008  (JP) .................................. 2008-267405

(51) Int. Cl.
*A61B 8/00* (2006.01)
(52) U.S. Cl.
USPC ............ 600/437; 600/438; 600/443; 600/407
(58) Field of Classification Search
None
See application file for complete search history.

(56) References Cited

U.S. PATENT DOCUMENTS 6,360,027 B1 * 3/2002 Hossack et al. ............... 382/294
8,066,644 B2 * 11/2011 Sarkar et al. .................. 600/461

FOREIGN PATENT DOCUMENTS

| JP | 5-253225 | 10/1993 |
|---|---|---|
| JP | 2001-198128 | 7/2001 |
| JP | 2002-95640 | 4/2002 |
| JP | 2005-279096 | 10/2005 |

OTHER PUBLICATIONS

Japanese Notice of Rejection Reasons issued Feb. 8, 2013, in Japan Patent Application No. 2008-267405 (with English translation).

* cited by examiner

*Primary Examiner* — Unsu Jung
*Assistant Examiner* — Joel Lamprecht
(74) *Attorney, Agent, or Firm* — Oblon, Spivak, McClelland, Maier & Neustadt, L.L.P.

(57) ABSTRACT

An ultrasound diagnosis apparatus that can perform predetermined input operations without using an operation table or a remote controller. To realize improved ergonomics in an ultrasound diagnosis apparatus, predetermined input operations, such as storing moving images or change of scanning mode, can be performed during examinations analyzing physical operations of an ultrasound probe from generated images. An image data analyzing unit acquires movement data of an ultrasound probe by analyzing image data generated by processing the received signals from the ultrasound probe. An operation converting unit converts the acquired movement data to a predetermined input operation data. A system control unit controls each of units in the ultrasound diagnosis apparatus based on the input operation data from the operation converting unit.

16 Claims, 10 Drawing Sheets

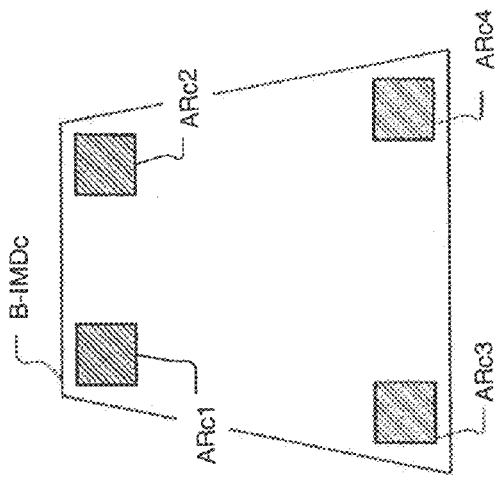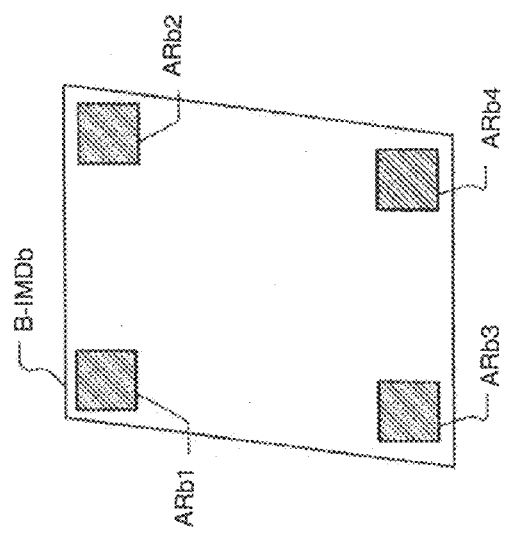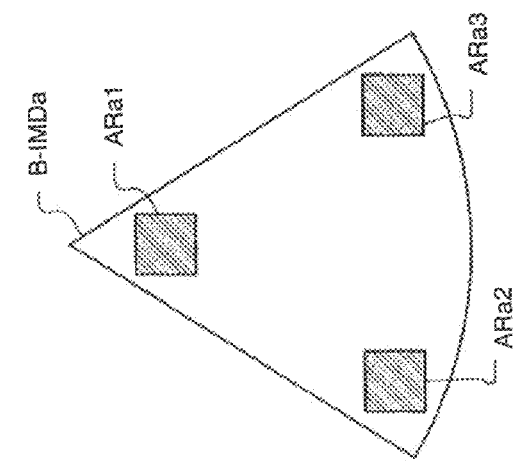

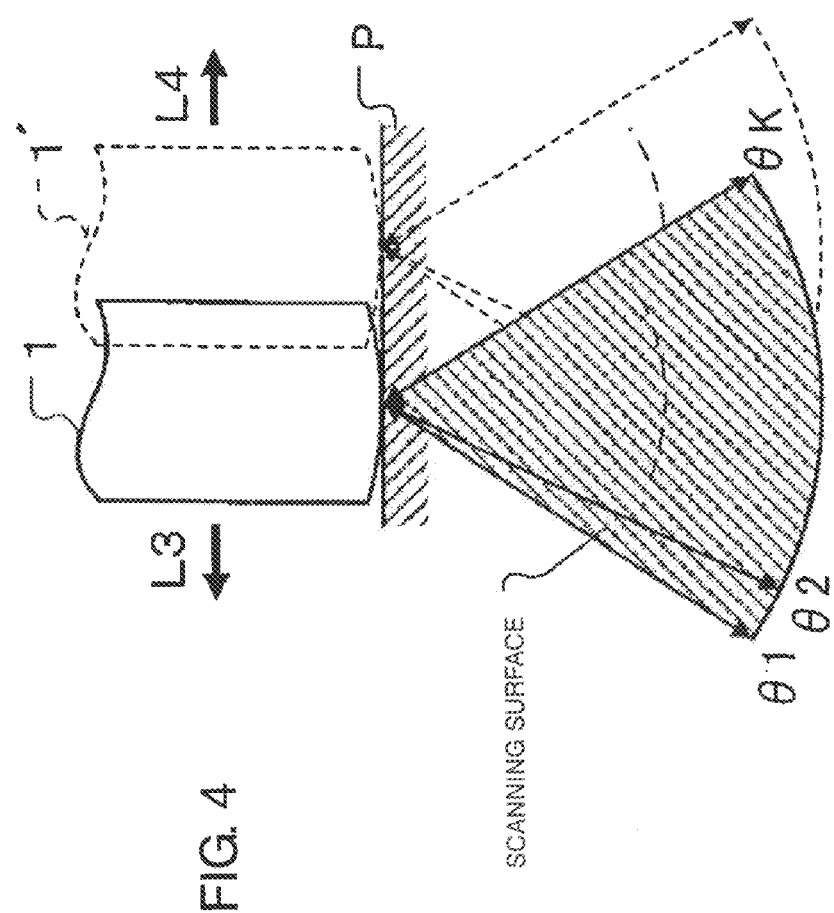

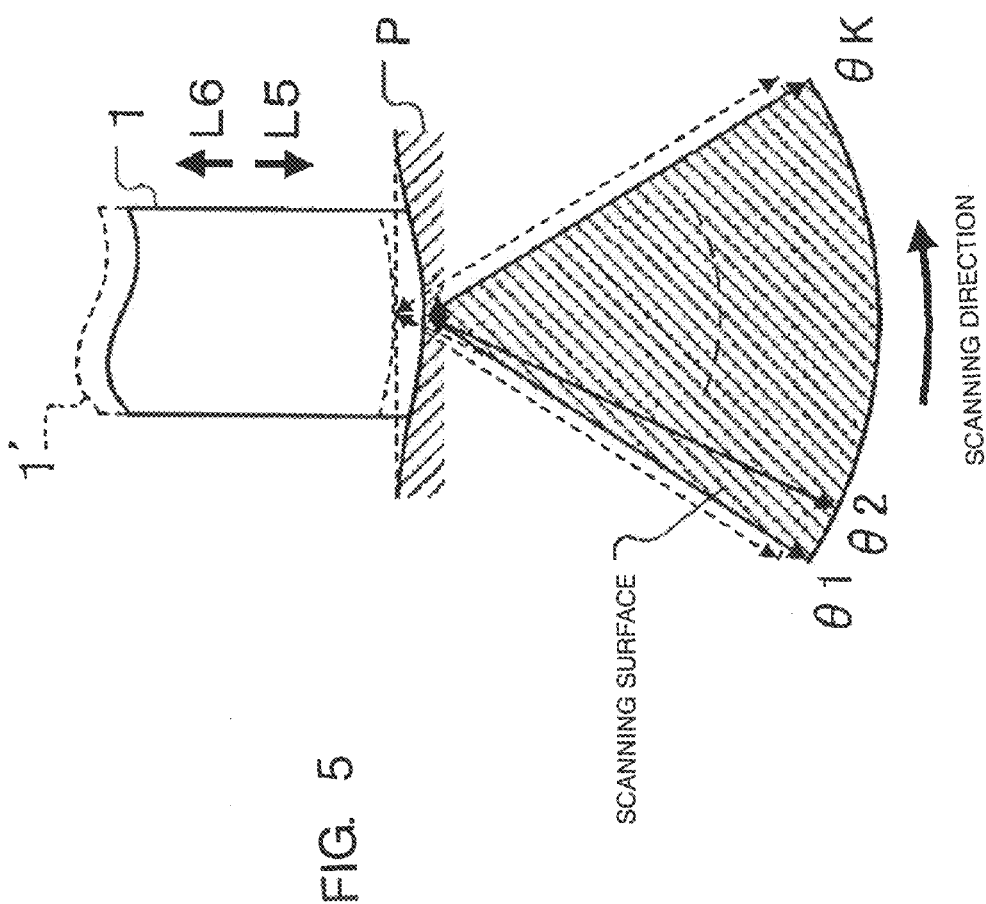

ULTRASOUND DIAGNOSIS APPARATUS

CROSS-REFERENCE TO RELATED APPLICATIONS

This application claims priority under 35 U.S.C. §119(a) from, and the benefit of, Japanese Patent Application No. 2008-267405, filed on Oct. 16, 2008, the contents of which are expressly incorporated herein by reference in their entirety.

BACKGROUND OF THE INVENTION

1. Field of the Invention

The present invention relates to an ultrasound diagnosis apparatus, and more particularly, an ultrasound diagnosis apparatus that can perform predetermined input operations, such as storing a moving image and changing a scanning mode without using an operation table, by analyzing and acquiring characteristics of physical operations of an ultrasound probe from generated images.

2. Background of the Invention

An ultrasound diagnosis apparatus transmits and receives ultrasound through a plurality of ultrasound transducers installed in an ultrasound probe to and from a target in an object. By simply touching an ultrasound probe to a patient's body surface, image data of the target is generated. The generated image data can be displayed on a monitor in real time. An ultrasound diagnosis apparatus is widely used as an apparatus for diagnosing various target organs in a patient's body, such as cardiology, vascular, urology or gynecology.

In an ultrasound diagnosis apparatus, to perform input operations for an examination, an operator operates input devices provided on an operation unit, such as various switches, touch panels, a mouse or a track ball, or a panel of a terminal device coupled to networks. Usually, while an operator of an ultrasound diagnosis apparatus holds an ultrasound probe with one hand to touch a tip portion of the ultrasound probe onto an object, the other hand of the operator performs input operations for an examination by operating an operation table.

However, to examine, for instance, peripheral blood vessels in a lower leg of an object through an ultrasound probe, an operator needs to step away from an operation table to adjust a position of an ultrasound probe around the lower leg or to adjust a body position of the object. Consequently, it is difficult for an operator to perform input operations on an operation table while adjusting a position of an ultrasound probe around a lower leg position of an object.

To address this problem, Japanese Patent Application Publication 2005-185420 has proposed an ultrasound diagnosis apparatus having a foot switch for performing an input operation and an ultrasound diagnosis apparatus that can perform input operation by voice recognitions.

However, it is difficult to perform fine operations by such a foot switch. Further, it is very physically and mentally fatiguing and uncomfortable for an operator to perform complicated input operations by a foot switch so as to avoid any error under a situation that both hands of the operator are occupied for other operations. Thus, such input operations by a foot switch are not desirable in view of ergonomics.

It is also very difficult to perform a plurality of complicated input operations by using voice recognition. To control such complicated input operations by voice recognition, an operator will need to issue various complicated commands. Further, there is the possibility of misunderstanding the voice input operation.

SUMMARY OF THE INVENTION

The present invention addresses the above-mentioned and other problems and drawbacks, and provides a novel ultrasound diagnosis apparatus with improved ergonomics that can perform predetermined input operations by an operator of an ultrasound probe during examination through the ultrasound probe without using an operation table or a remote controller.

Thus, an ultrasound diagnosis apparatus according to the present invention analyzes physical operation effects of an ultrasound probe from generated images. By acquiring characteristics among the analyzed operation effects, the ultrasound diagnosis apparatus automatically performs predetermined input operations, such as storing a moving image, or changing a scan mode.

The ultrasound diagnosis apparatus according to one embodiment of the present invention includes:

(1) an ultrasound probe including a plurality of transducers to emit and receive ultrasounds;

(2) an operation unit to input data for performing examination of an object;

(3) a transmission/reception unit to supply driving signals to a prescribed number of transducers in the plurality of transducers for scanning ultrasounds on the object and to convert ultrasound reflected from the object into receiving signals;

(4) an image data generating unit to generate B mode image data by processing the receiving signals supplied from the transmission/reception unit;

(5) an image data analyzing unit to analyze a whole area of the B mode image data generated by the image data generating unit or a plurality of analyzing regions provided at each adjacent view corner of the B mode image data to acquire movement data of the ultrasound probe; and (6) an operation conversion unit configured to convert the movement data of the ultrasound probe to a predetermined operation data for the operation unit.

It is to be understood that both the forgoing description and the following more detailed description are exemplary, and are not restrictive of claim scope.

BRIEF DESCRIPTION OF THE DRAWINGS

The accompanying drawings, which are incorporated in and constitute part of this specification, illustrate various embodiments and/or features of embodiments of the present invention, and together with the description, serve to explain embodiments of the present invention. Where possible, the same reference numbers are used throughout the drawings to describe the same or like parts. In the drawings:

FIGS. 3A-3C illustrate examples of a plurality of rectangular analyzing regions provided near a plurality of corners of an outline for a generated B mode image data to acquire movement data of an ultrasound probe in an embodiment consistent with the present invention.

FIG. 4 illustrates movement data of an ultrasound probe with moving a scan surface of an ultrasound probe parallel to a body surface of an object in an embodiment consistent with the present invention.

FIG. 5 illustrates pressurization movement data and depressurization movement data of an ultrasound probe with moving a scan surface of an ultrasound probe parallel to a body surface of an object in an embodiment consistent with the present invention.

DESCRIPTION OF PREFERRED EMBODIMENTS

The present invention provides an ultrasound diagnosis apparatus that can perform predetermined input operations, such as storing moving images and changing a scanning mode by analyzing physical operations of an ultrasound probe and acquiring characteristics of the movement from a generated image. According to an ultrasound diagnosis apparatus consistent with the present invention, while both hands of an operator for an ultrasound probe are occupied, it becomes possible for an operator to perform predetermined input operations by moving the ultrasound probe without using an operation table or a remote controller. Thus, the present invention provides an ultrasound diagnosis apparatus with improved ergonomics.

Figure 1:
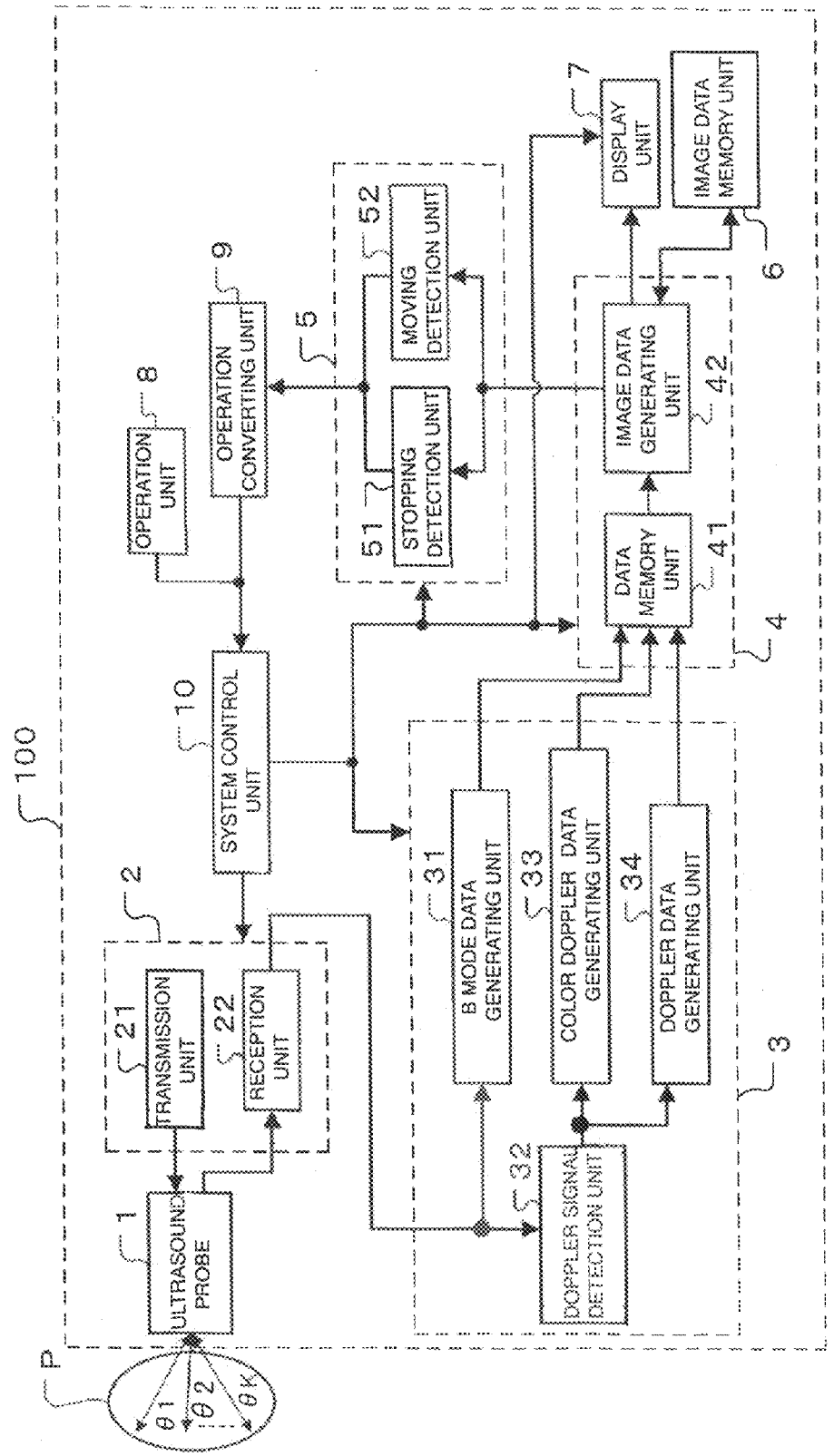
FIG. 1 is a block diagram illustrating an ultrasound diagnosis apparatus in accordance with preferred embodiments of the present invention.

FIG. 1 is a block diagram illustrating an ultrasound diagnosis apparatus in accordance with preferred embodiments of the present invention. The ultrasound diagnosis apparatus 100 includes an ultrasound probe 1, a transmission/reception unit 2, a data generating unit 3 and an image data processing unit 4. The ultrasound probe 1 transmits and receives ultrasounds to and from an object P of a target for examination. The transmission/reception unit 2 scans ultrasounds on the object P by driving the ultrasound probe 1. The data generating unit 3 generates B mode data or color Doppler data by processing the received signals from the transmission/reception unit 2. The image data processing unit 4 generates image data, such as B mode image data or color Doppler image (CDI) data, by processing B mode data or color Doppler data generated in the generating unit 3.

The ultrasound diagnosis apparatus 100 further includes an image data analyzing unit 5, an image data memory unit 6, a display unit 7, an operation unit 8, an operation converting unit 9 and a system control unit 10. The image data analyzing unit 6 analyzes image data generated in the image data processing unit 4 to acquire movement data of the ultrasound probe 1. The image data memory unit 6 stores image data generated in the image data processing unit 4. The display unit 7 displays image data generated in the image data processing unit 4. The operation unit 8 inputs operation data for performing examination of an object P. The operation converting unit 9 converts the movement data of the ultrasound probe 1 acquired in the image data analyzing unit 5 into operation data to be input to the system control unit 10 with data from the operation unit 8. The system control unit 10 totally controls each of the units in the ultrasound diagnosis apparatus 100 based on the operation data supplied from the operation unit 8 and the operation converting unit 9.

Ultrasound transmission/reception are performed by contacting a tip surface of the ultrasound probe 1 onto a body surface of an object P. In the tip portion of the ultrasound probe, a plurality (N) of transducers is, for example, linearly arranged. Each of the plurality of transducers is coupled to the transmission/reception unit 2 through each of a plurality of cables. By driving selected transducers through driving signals supplied from the transmission/reception unit 2, transmitting ultrasound pulses are transmitted onto the object P. The selected transducers receive echo ultrasounds from the object P and convert received ultrasound signals to supply the received signals to the transmission/reception unit 2 through the cables.

The transmission/reception unit 2 includes a transmission unit 21 and a reception unit 22. The transmission unit 21 generates driving signals for driving the selected transducers in the ultrasound probe 1 to transmit ultrasounds. The reception unit 22 performs a delaying and summing of the receiving signals acquired through the selected receiving transducers in the ultrasound probe 1.

The transmission unit 21 includes a rate pulse generating unit, a transmission delay circuit, and a plurality of channels driving circuit (all not shown). The rate pulse generating unit generates rate pulses for determining a repetition cycle (Tr) of the transmission ultrasounds by dividing a reference signal supplied from the system control unit 10. The transmission delay circuit includes a plurality of channels of independent delay circuits and gives focusing delay times for focusing the transmission ultrasound at a prescribed depth distance, and deflecting delay times for emitting transmission ultrasounds to the generated rate pulse. The plurality of channels driving circuit generates driving pulses for driving the plurality of transmitting transducers based on the delayed rate pulse.

The reception unit 22 includes a plurality of pre-amplifiers, and a plurality of receiving delay and summation units (all not shown). The pre-amplifiers amplify the received signals of a selected plurality of channels supplied from the receiving transducers in the ultrasound probe 1 to maintain a sufficient S/N ratio. Each of the receiving delay and summation units includes a reception delay circuit and a summation circuit for summing the received signals of the selected plurality of channels by providing deflection delay times for setting a strong receiving directivity to each of the plurality of parallel simultaneous reception beam directions located in the transmission beam acoustic field and by providing the focusing delay times for focusing the reception ultrasounds from a prescribed depth. The summed received signal is supplied to the data generating unit 3.

The data generating unit 3 includes a B mode data generating unit 31, a Doppler signal detection unit 32, a color Doppler data generating unit 33 and a Doppler data generating unit 34. The B mode data generating unit 31 generates B mode data, color Doppler data and Doppler spectrum data from the receiving signals output from the reception unit 22 in the transmission/reception unit 2.

The B mode data generating unit 31 in the data generating unit 3 includes a logarithmic converter, an envelope detector and an A/D converter (all not shown). The logarithmic converter 412 generates B mode data for the respective parallel simultaneous reception beam directions by emphasizing relative small amplitude signals of the envelope detected receiving signals output from the reception unit 22. The generated B mode data is output to the image data processing unit 4.

The Doppler signal detection unit 32 includes a π/2 phase converter, a plurality of mixers, and a plurality of low pass filters (LPFs) (all not shown). The Doppler signal detection unit 32 detects Doppler signals by performing orthogonal phase detection of the received signals output from the reception unit 22.

The color Doppler data generating unit 33 in the color data generating unit 3 generates color Doppler data based on the Doppler signals detected in the Doppler signal detection unit 32. The color Doppler data generating unit 33 includes an A/D converter, a filter of a high band pass digital filter and an auto-correlation computing unit (all not shown). The A/D converter converts Doppler signals output from the Doppler signal detection unit 32. The filter circuit reads the complex signals stored in the Doppler signal memory unit and eliminates Doppler components (clatter components) in the complex signals due to influences of the movement of organs, such as movement due to breathing or heart beats. The auto-correlation computing unit computes an auto-correlation value to the Doppler component in the extracted blood data and further generates color Doppler data for each of the parallel simultaneous reception beam directions by computing a mean flow value of the blood flow, a variance value and a power value based on the auto-correlation value. The computed blood flow data is supplied to the image data processing unit 4 as color Doppler data.

The Doppler data generating unit 34 in the data generating unit 3 generates Doppler spectrum data based on the Doppler signals detected by the Doppler signal detection unit 32. The Doppler data generating unit 34 includes a sample hold circuit, a high band pass filter (HPF), an A/D converter and a fast Fourier transformer (FFT). The Doppler data generating unit 34 generates Doppler spectrum data by converting Doppler signals output from the Doppler signal detection unit 32 by the sampling pulses supplied from the system control unit 10 after eliminating noise components. The generated Doppler spectrum data is supplied to the image data processing unit 4.

The image data processing unit 4 includes a data memory unit 41 and an image data generating unit 42. The data memory unit 41 stores B mode data output from the B mode data generating unit 31 in the data generating unit 3, color Doppler (CD) data output from the color Doppler data generating unit 33 and Doppler spectrum data (Pulse Wave Doppler data (PWD) output from the Doppler data generating unit 34.

The image data generating unit 42 in the image data processing unit 4 reads B mode data, color Doppler (CD) data and Doppler spectrum data (PWD) respectively stored in the data memory unit 41 and generates each of B mode image data, color Doppler image (CDI) data and Doppler spectrum data (PWD) image data, respectively.

The image data generating unit 42 reads B mode data stored in the data memory unit 41. By performing coordinate conversion to the read B mode data, the image data generating unit 42 generates B mode image data constructed by pixels each having a brightness in accordance with a strength of an echo ultrasound along at each of depth directions θ1-θK in an object P. The generated B mode image data is supplied to the image data analyzing unit 5 and the display unit 7.

Next, the image data generating unit 42 reads out color Doppler data stored in the data memory unit 41 and generates color Doppler image (CDI) data for color indicating blood flow direction or flow speed in an object P by performing coordinate conversion of the read out color Doppler data. The generated CDI data is overlapped on a region of interest (ROI) of the previously generated B mode image data. The overlapped (B+CDI) image data is output to the display unit 7.

Further, the image data generating unit 42 reads out Doppler spectrum data stored in the data memory unit 41 and generates PWD image data for representing temporal changes of blood flow speed based on the read out Doppler spectrum (PWD) data. The generated PWD image data is overlapped on the previously generated B mode image data. The overlapped (B+PWD) image data is displayed on the display unit 7. Still further, the generated PWD image data is overlapped on the (B+CDI) image data. The overlapped (B+CDI+PWD) image data is output to the display unit 7.

The image data analyzing unit 5 analyzes two neighboring B mode image data generated from the image data generating unit 42 to detect movement data of the ultrasound probe 1 at a time when the image data is generated. The image data analyzing unit 5 includes a stopping detection unit 51 and a moving detection unit 52. The stopping detection unit 51 acquires a stop data for indicating a status that the ultrasound probe 1 is stopped with contacting to an object P as a one of the movement data based on each brightness value of pixels in a whole area of the two neighboring B mode image data generated in time series from the image data generating unit 42, or each brightness value of pixels in a whole area of the neighboring B mode image data that are thinned out at a prescribed thin out ratio.

Thus, the stopping detection unit 51 acquires a pixel number greater than the prescribed threshold by performing, for example, a binary coding process at a prescribed threshold and a shape matching process for each of neighboring two B mode image data generated in time series. When the shapes are substantially coincided and the acquired pixel number is greater than a certain ratio, the stopping detection unit 51 judges that the ultrasound probe 1 is stopped, and outputs a stop data to the operation converting unit 9.

The moving detection unit 52 analyzes changes of brightness values of two neighboring B mode image data generated in time series from the image data generating unit 42 in the image data processing unit 4, or changes of brightness values of two neighboring B mode image data thinned out at an interval of a prescribed thin out ratio to acquire movement data of the ultrasound probe 1. The acquired movement data is output to the operation converting unit 9.

Figure 2:
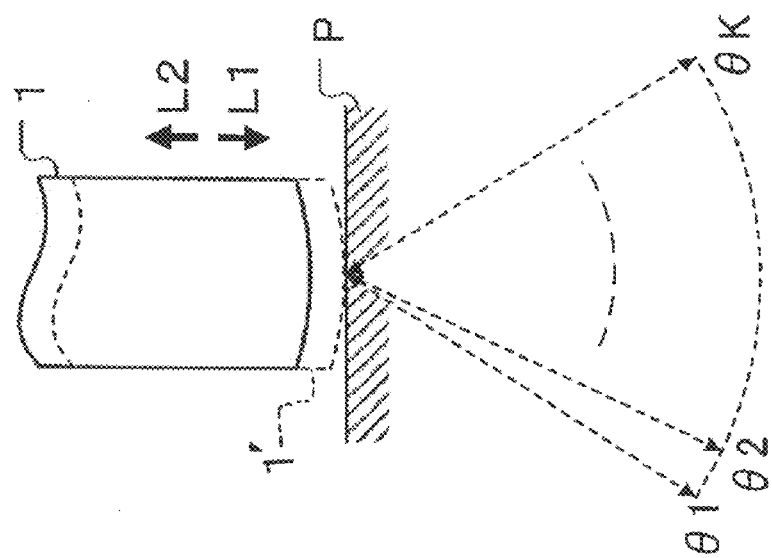
FIG. 2 illustrates upward movement data of an ultrasound probe for moving from a contacting position on an object to an air position, or vice versa downward movement data of the ultrasound probe, in an embodiment consistent with the present invention.

When the movement data of the ultrasound probe includes pixels in a whole area of one image data of the two neighboring B mode data generated in time series less than the imaging threshold amount and the other image data includes pixels greater than the imaging threshold amount, the moving detection unit 52 judges that when the one image data is generated, a tip portion of the ultrasound probe 1 is located in air such that it is impossible to perform transmission/reception of the ultrasounds, as shown by the solid line in FIG. 2. When the moving detection unit 52 outputs the judging signal that the tip portion of the ultrasound probe 1 is located in the air, the operation converting unit 9 acquires a moving direction from a position of the ultrasound probe 1 above an object P to a contacting position onto the object P (FIG. 2, the arrow L1 direction).

On the other hand, when other image data including pixels greater than the imaging threshold amount is generated, the moving detection unit 52 judges that the tip portion of the ultrasound probe 1 is in contact with the object P, as illustrated by the dashed line in FIG. 2. When the moving detection unit 52 outputs a judging signal that the tip portion of the ultrasound probe 1 is in contact with the object P, the operation converting unit 9 acquires a moving direction of the ultrasound probe 1 from the contacting position to the object P to a position above the object P (FIG. 2, the arrow L2 direction).

The operation converting unit 9 acquires movement data of a moving direction and a moving distance of the ultrasound probe by analyzing operations of the ultrasound probe 1 at a plurality of rectangular analyzing regions provided under a prescribed algorithm around or near each corner of an outline of the B mode image data. FIG. 3A illustrates a B mode image data (B-IMDa) of a fan shaped outline of viewing scope. Near each corner of the fan shaped outline of B mode image data (B-IMDa), three rectangular analyzing regions ARa1, ARa2 and ARa3 are provided under a prescribed algorithm. FIG. 3B illustrates B mode image data (B-IMDb) of a parallelogram outline. FIG. 3C illustrates B mode image data (B-IMDc) of a trapezoidal outline. In each of the corners of the respective outlines B-IMDb and B-IMDc, four rectangular analyzing regions (ARb1, ARb2, ARb3, ARb4) and four rectangular analyzing regions (ARc1, ARc2, ARc3, ARc4) are respectively provided under a prescribed algorithm.

The operation converting unit 9 acquires movement data of the ultrasound probe 1 moving at a contacting state to the object P based on changes of brightness values in accordance with moving operations of the ultrasound probe at the plurality of rectangular analyzing regions AR provided near each corner of the outline of the B mode image data B-IMD by applying, for example, a gradient method or a block matching method.

When all of the moving directions acquired from the three rectangular analyzing regions ARa1, ARa2 and ARa3 provided at each corner of the fan shaped B mode image data B-IMDa are in the same direction, the operation converting unit 9 acquires moving direction data of the ultrasound probe 1. Similarly, when all of the moving directions acquired from the four rectangular analyzing regions ARb1, ARb2, ARb3 and ARb4 provided at each corner of the B mode image data B-IMDb and all of the moving directions acquired from the four rectangular analyzing regions ARc1, ARc2, ARc3 and ARc4 provided at each corner of the B mode image data B-IMDc are respectively in the same direction, the operation converting unit 9 acquires moving direction data of the ultrasound probe 1.

FIG. 4 illustrates parallel movements of an ultrasound probe 1 along a scan surface formed by ultrasound scans by the transmission/reception unit 2 in a left (an arrow L3) direction or a right (an arrow L4) direction on a body surface of an object P. When all moving directions of the ultrasound probe acquired from the plurality of rectangular analyzing regions provided near the plurality corners of an outline of B mode image data are in the same L3 or L4 direction, the operation converting unit 9 acquires a moving distance to the left or the right moving direction.

FIG. 5 illustrates movements of a scan surface of the ultrasound probe in contact with a body surface of an object P in an arrow L5 direction for pressurizing or pressing against the body surface or an arrow L6 direction for depressurizing or lessening pressing against the body surface. When all moving directions of the ultrasound probe acquired from the plurality of rectangular analyzing regions provided near the plurality corners of an outline of B mode image data are in the same L5 or L6 direction, the operation converting unit 9 acquires a moving distance toward the air (upward) direction or a body contacting (downward) direction of the moving direction.

If a moving portion of an imaging target for the ultrasound diagnosis, such as a heart, is included into the plurality of rectangular analyzing regions, it becomes difficult to correctly acquire the moving direction data of the ultrasound probe from the plurality of rectangular analyzing regions. Consequently, it is desired to set the plurality of analyzing regions AR near each corner of an outline of the B mode image data. Usually, an ultrasound probe is operated so as that an imaging target portion for the ultrasound diagnosis is located at or around the center of the B mode image data.

Referring to FIG. 1, the image data memory unit 6 includes a memory device, such as a magnetic disk. The image data memory unit 6 stores image data generated from the image data generating unit 42 in the image data processing unit 4 based on operation data output from the operation unit 8 or the operation converting unit 9 through the system control unit 10.

The display unit 7 includes a monitor such as a liquid crystal panel (LCP) or a cathode ray tube (CRT) to display image data output from the image data generating unit 42 in the image data processing unit 4. Thus, image data such as B mode image data (B-IMD), (B+CDI) image data, (B+PWD) image data or (B+CDI+PWD) image data is displayed on the monitor. The display unit 7 further displays an operation menu having operation keys to input operation data from the operation unit 8 or the operation converting unit 9.

The operation unit 8 includes input devices such as a plurality of switches, ten-keys, a touch panel, a pointing device (a mouse or a trackball, etc.). By using these input devices, operation data, such as an object data, imaging condition setting data, image data storing data, etc. are input. The object data includes an identification (ID) and name of an object. The imaging condition setting data includes operation data for setting a gain, a frequency of the transmission/reception, a focusing position, a pulse repeating frequency, a viewing depth, a frame rate and a generation mode of the image data.

The operation unit 8 further supplies operation data, such as operation data for storing image data generated from the image data generating unit 42 in the image data processing unit 4, operation data for displaying operation menu on the display unit 7, operation data for moving a cursor onto each of operation keys in an operation menu displayed on the display unit 7, and operation data for setting an imaging condition by pressing the operation key at the cursor position in the operation menu displayed in the display unit 7 to the system control unit 10.

The operation converting unit 9 converts stop data output from the stopping detection unit 51 in the image data analyzing unit 5, the moving direction output from the moving detection unit 52, and each movement data of the moving direction and the moving distance output from the moving detection unit 52 in accordance with the operation of the ultrasound probe 1 to the prescribed operation data that is the same operation data input through the operation unit 8. The converted operation data is supplied to the system control unit 10.

Data in accordance with the operation of the ultrasound probe is converted into operation data in the operation converting unit 9. For instance, in accordance with an operation for stopping the ultrasound probe while contacting an object P, the stopping detection unit 51 outputs a stop data. The output stop data is converted into an operation time data for displaying the stop time of the ultrasound probe 1 in the operation converting unit 9. The converted operation time data is output to the system control unit 10. In the system control unit 10, the stop time period of the ultrasound probe is calculated based on the operation time data output from the operation converting unit 9.

When the ultrasound probe 1 is stopped while contacting the object P in a prescribed time period, for instance, five (5) seconds, the moving detection unit 52 outputs stopping time data in response to the storing stop operation. When the stopping time data is output and the prescribed time period, i.e., the five (5) seconds, has passed, the operation converting unit 9 converts the image data generated in the image data generating unit 42 to the operation data for storing the image data into the image data memory unit 6.

FIG. 2 illustrates an embodiment of a first operation that converts the operation of the ultrasound probe 1 into a display or a non-display of the operation menu based on detecting certain exemplary movements of the ultrasound probe. In this embodiment of the first moving operation of the ultrasound probe, the ultrasound probe is operated so as to repeatedly reciprocate in both directions for contacting and pressing against the body surface of the object P (L1 direction) and for non-contacting in the air above (L2 direction) the body surface during a prescribed time period, for instance two (2) seconds. In accordance with the first moving operation of the ultrasound probe, the moving detection unit 52 outputs moving direction data. The output moving direction data is converted into the first operation data in the operation converting unit 9. The first operation data drives the operation unit 7 so as to display an operation menu on the display unit 7 or to prohibit displaying the operation menu.

Figure 6:
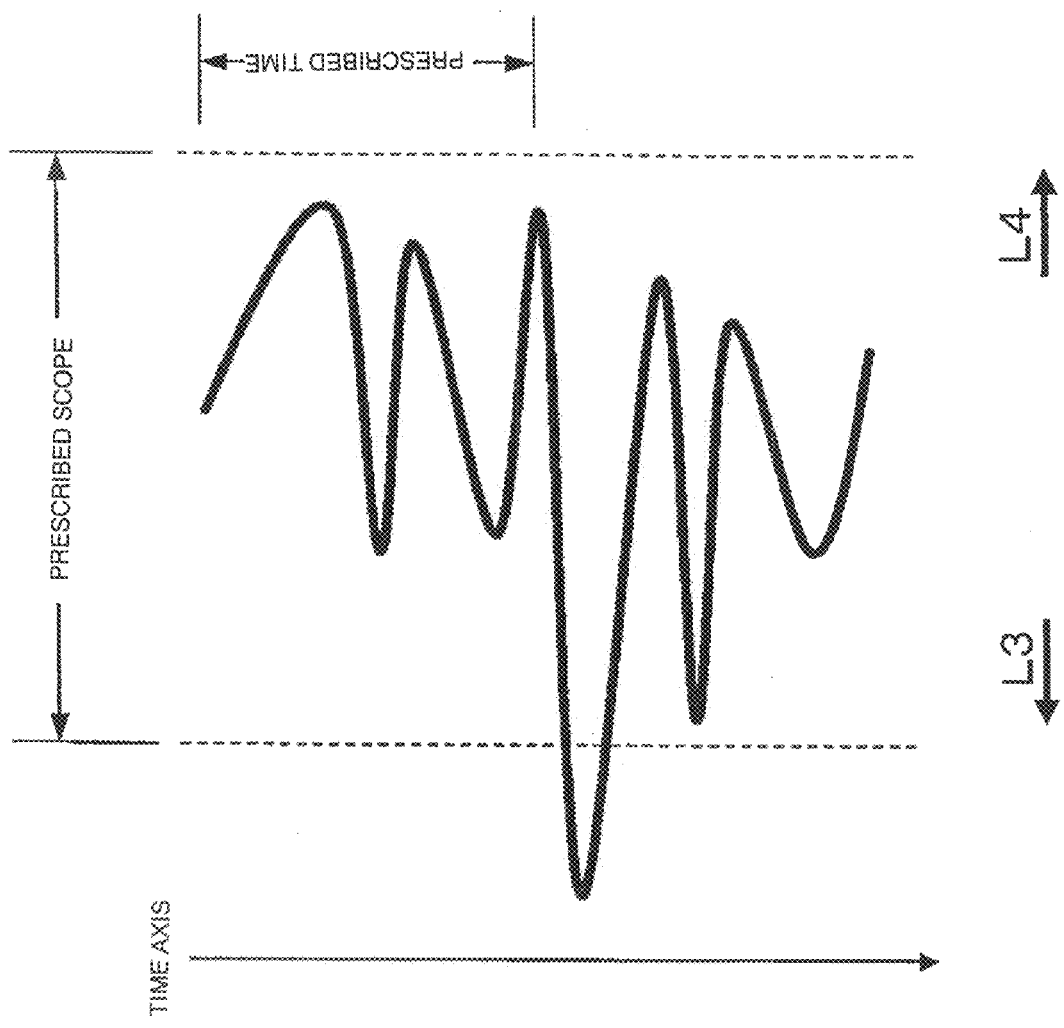
FIG. 6 illustrates an embodiment for performing a menu changing operation by detecting movement data of an ultrasound probe in an ultrasound diagnosis apparatus consistent with the present invention.

FIG. 6 illustrates an embodiment of a second operation for converting the operation of the ultrasound probe 1 into an operation for moving the cursor in the operation menu based on detecting certain exemplary movements of the ultrasound probe. In this second moving operation, the ultrasound probe 1 is wiggled in, for example, a left (L3) direction and a right (L4) direction on the body surface of an object P. Thus, after repeating a plurality of wiggles during a prescribed time period (AT), for instance one (1) second, in a prescribed region (AR), the ultrasound probe 1 is largely moved outside of the prescribed region (AR). When the moving detection unit 52 outputs moving direction data and moving distance data in accordance with this second moving operation of the ultrasound probe 1, the operation converting unit 9 converts the second moving operation of the ultrasound probe to the second operation data for moving the cursor for the operation menu displayed display unit 7 onto an operation key positioned in one direction.

FIG. 5 illustrates an embodiment of a third operation for converting the operation of the ultrasound probe 1 into an operation for setting imaging conditions by pressing the operation key based on detecting certain exemplary movements of the ultrasound probe. In the third operation of the ultrasound probe, the ultrasound probe 1 is moved up and down during a prescribed time period, for instance one (1) second, with contacting to the body surface of the object P. Thus, the ultrasound probe 1 is moved repeatedly in a reciprocated operation in the pressurizing or pressing against (L5) direction and the depressurizing or moving away from (L6) direction in a predetermined time, for instance more than two (2) times. When the moving detection unit 52 outputs moving direction data in accordance with this third moving operation of the ultrasound probe 1, the operation converting unit 9 converts the third moving operation of the ultrasound probe to the third operation data for setting imaging conditions by pressing the operation key by pressing the operation key at the cursor position in the operation menu.

FIGS. 4 and 5 explain the conversions to fourth and fifth operation data for setting X and Y coordinates of a region of interest (ROI) for the (B+CDI) image data based on detecting certain exemplary movements of the ultrasound probe. As shown in FIG. 4, the ultrasound probe 1 is wiggled along the left (L3) and the right (L4) directions in the prescribed region AR. After wiggling in a prescribed region AR, the ultrasound probe 1 is moved outside of the prescribed region AR in either the L3 or L4 direction. In accordance with this moving operation of the ultrasound probe, the moving detection unit 52 outputs the moving direction data and the moving distance data. The operation converting unit 9 converts these data output from the moving detection unit 52 to the fourth operation data for moving the direction of the coordinate of the ROI along one direction on the X-axis of the ROI.

As shown in FIG. 5, the ultrasound probe 1 is reciprocated in a pressurizing or pressing against (L5) direction and a depressurizing or lessening pressing against (L6) direction while contacting the body surface of the object P within the prescribed region AR. After wiggling in L5 and L6 directions in the prescribed region AR, the ultrasound probe is moved along the pressurizing or pressing against direction or the depressurizing or lessening pressing against direction. In accordance with the moving operation, the moving detection unit 52 outputs the moving direction data and the moving distance data. The operation converting unit 9 converts the moving direction data and the moving distance data to the fifth operation data for moving the coordinate of Y-axis of the ROI that is orthogonal to the X-axis in one direction along the Y-axis.

It is possible to adjust the locus of the moving direction and the moving distance of the ultrasound probe 1. The locus of the moving direction and the moving distance of the ultrasound probe are displayed on the display unit 7. Based on the moving locus, the adjustment is performed by multiplying a prescribed coefficient to the moving distance so as to match the operation of an operator. Further, it is possible to set a high thinning out ratio for an operator who cannot quickly move the ultrasound probe 1 or when the frame rate of the imaging condition is highly set.

The system control unit 10 includes a central processing unit (CPU) and a memory circuit. An object data and the operation data output from the operation unit 8 and the operation data output from the operation converting unit 9 are stored in the memory circuit of the system control unit 10. The system control unit 10 totally controls each unit of the transmission/reception unit 2, the data generating unit 3, the image data processing unit 4, the image data analyzing unit 5 and the display unit 7, based on the stored operation data.

Figure 7:
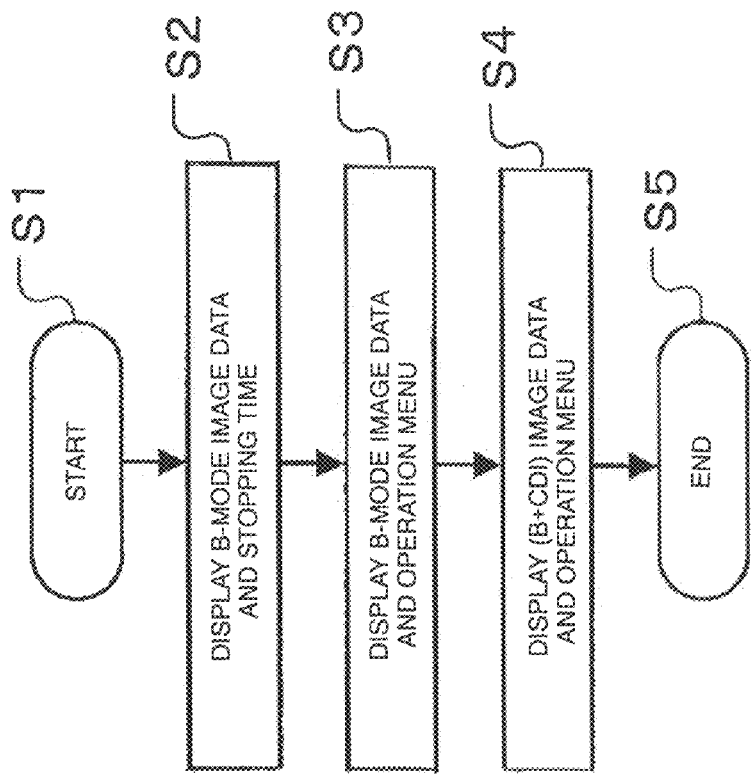
FIG. 7 is a flowchart for illustrating operations of an ultrasound diagnosis apparatus consistent with the present invention.

FIG. 7 is a flowchart illustrating operations of the ultrasound diagnosis apparatus consistent with the present invention. The memory circuit of the system control unit 10, for example, stores an object data for performing examination of an object, operation data for generating B mode image data, and data of thin up ratio 0%.

An operator of the ultrasound diagnosis apparatus 100 starts the examination of the object by operating the operation unit by using one hand and holding the ultrasound probe with the other hand (FIG. 7, step S1).

When the examination start signal is supplied to the data generating unit 3 from the operation unit 8 through the system control unit, the B mode data generating unit 31 generates B mode data by processing the received signals output from the reception unit 22 in the transmission/reception unit 2 with contacting the tip portion of the ultrasound probe 1 to the object P. The generated B mode image data are successively stored in the data memory unit 41 of the image data processing unit 4. The stored B mode data is read out by the image data generating unit 42 in the image data processing unit 4 to generate B mode image data. The generated B mode image data is output to the display unit 7 and the image data analyzing unit 5.

The B mode image data output from the image data generating unit 42 is displayed in real time on the display unit 7.

B mode image data generated in time series from the image data generating unit 42 are analyzed by the stop detection unit 51 and the moving detection unit 52 in the image data analyzing unit 5 and acquired stop time data and movement data (moving direction data and moving distance data) of the ultrasound probe 1.

When a desired B mode image data is displayed on the display unit 7, while one hand of an operator holds near a target imaging position of an object P, the other hand of the operator stops the ultrasound probe 1 while contacting the object P. Under the stop status, the stop detection unit 51 in the image data analyzing unit 5 analyzes two neighboring B mode image data generated in time series from the image data generating unit 42 to acquire stop time data. The acquired stop time data is output to the operation converting unit 9.

The operation converting unit 9 converts the stop time data output from the stop detection unit 51 to time operation data. The converted time operation data is output to the system control unit 10. The system control unit 10 calculates a stop time of the ultrasound probe 1 based on the time operation data supplied from the operation converting unit 9.

The calculated stop time is supplied to the image data generating unit 42 in the image data processing unit 4 and output to the display unit 7 together with the generated B mode image data. Thus, both B mode image data output from the image data generating unit 42 and the stop time are displayed on the display unit 7 (FIG. 7, step S2).

Figure 8:
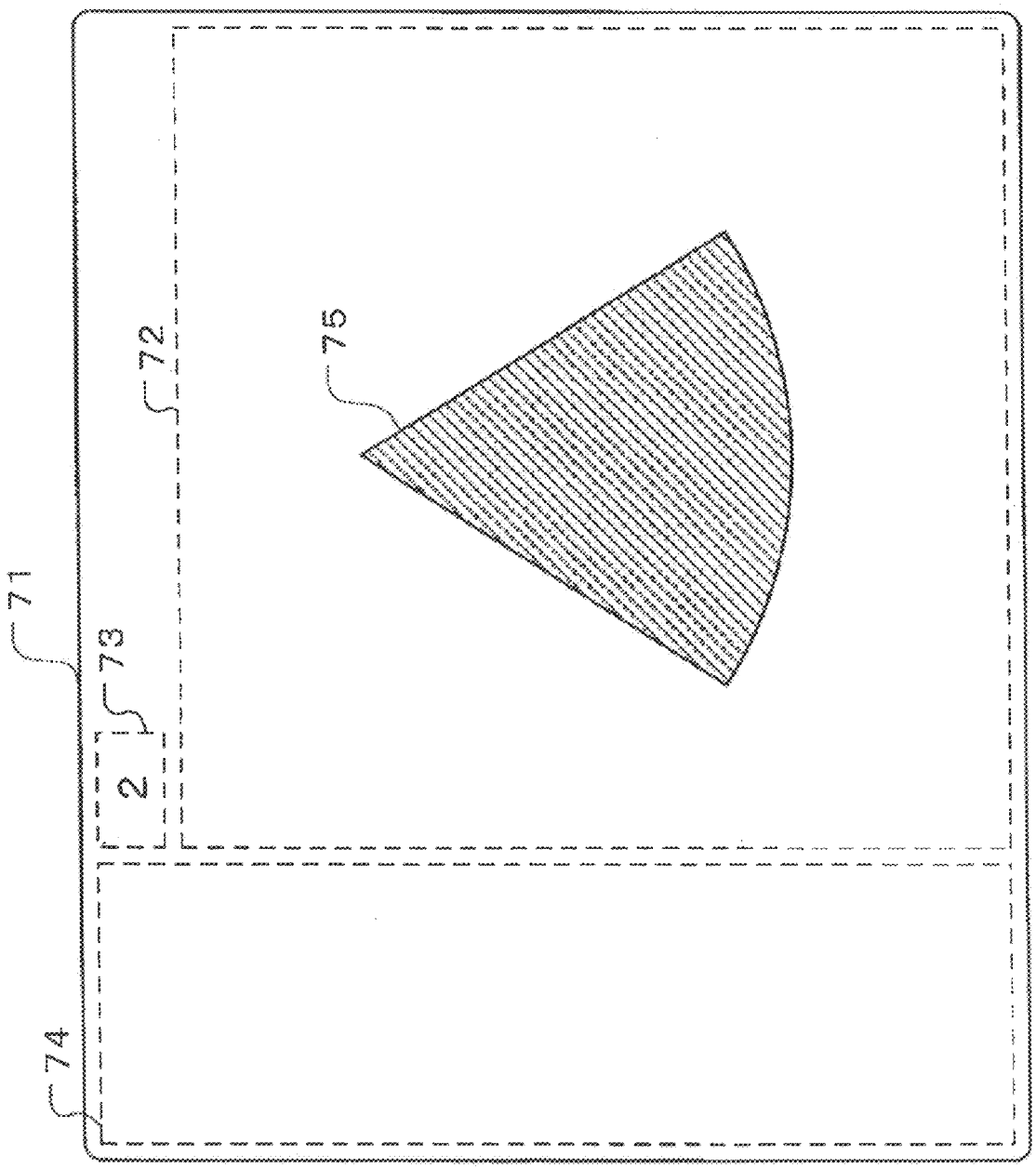
FIG. 8 illustrates an embodiment of B mode image data and a stop time period that are displayed on a display unit in the ultrasound diagnosis apparatus in accordance with analysis of movement of an ultrasound probe.

FIG. 8 illustrates an example display screen of the display unit 7 for displaying B mode image data and the stop time. In this example display, the display screen 71 includes a first display area 72 for displaying B mode image data 75 in real time, a second display area 73 for displaying the stop time of the ultrasound probe in real time detected and calculated in the operation converting unit 9, and a third display area 74 for displaying the operation menu.

In this example shown in FIG. 8, the stop time of the ultrasound probe displays a number "2" in real time. This shows a present time that a prescribed time period for example "5" is now counted down from the beginning of the stop operation of the ultrasound probe. Thus, in this example three seconds have passed from the beginning of the stop operation of the ultrasound probe. If another two seconds pass from this stop time, the second display area 73 displays a time "0".

In accordance with the stop operation of the ultrasound probe 1, the operation converting unit 9 converts the stop data output from the stop detecting unit 51 in the image data analyzing unit 5 to the storing operation data to supply the stop data to the system control unit 10. Based on the storing operation data supplied from the operation converting unit 9, the system control unit 10 stores the B mode image data generated in the image data generating unit 42 in the image data memory unit 6 when the number zero ("0") is displayed in the second display area 73.

Thus, the stop time data is acquired in accordance with the stop operation of the ultrasound probe 1. And by converting the acquired stop time data to the time operation data, it can display the B mode image data 75 in real time at the first display area 72 of the screen 71. At the same time, the stop time of the ultrasound probe 1 also can be displayed in real time in the second display area 73.

Further, it is possible to store the image data generated in the image data generating unit 42 to the image data memory unit 6 by acquiring storing data in accordance with the stop operation of the ultrasound probe and by converting the acquired storing data to the storing operation data.

By doing the above, while both hands of an operator are occupied, it is easy for the operator to perform such input operations by simply stopping or wiggling the ultrasound probe, similar to operations performed through the operation unit 8.

As mentioned above, the first moving operation of the ultrasound probe can be performed to display the operation menu on the display unit 7. In accordance with first moving operation of the ultrasound probe, the operation converting unit 9 converts the moving direction data output from the moving detection unit 52 in the image data analyzing unit 5 to the first operation data for driving the operation menu to be displayed on the display unit 7. Based on the first operation data output from the operation converting unit 9, the system control unit 10 displays the B mode image data and the operation menu generated from the generated image data generating unit 42 in the third display area 74 (FIG. 7, step S3).

Figure 9:
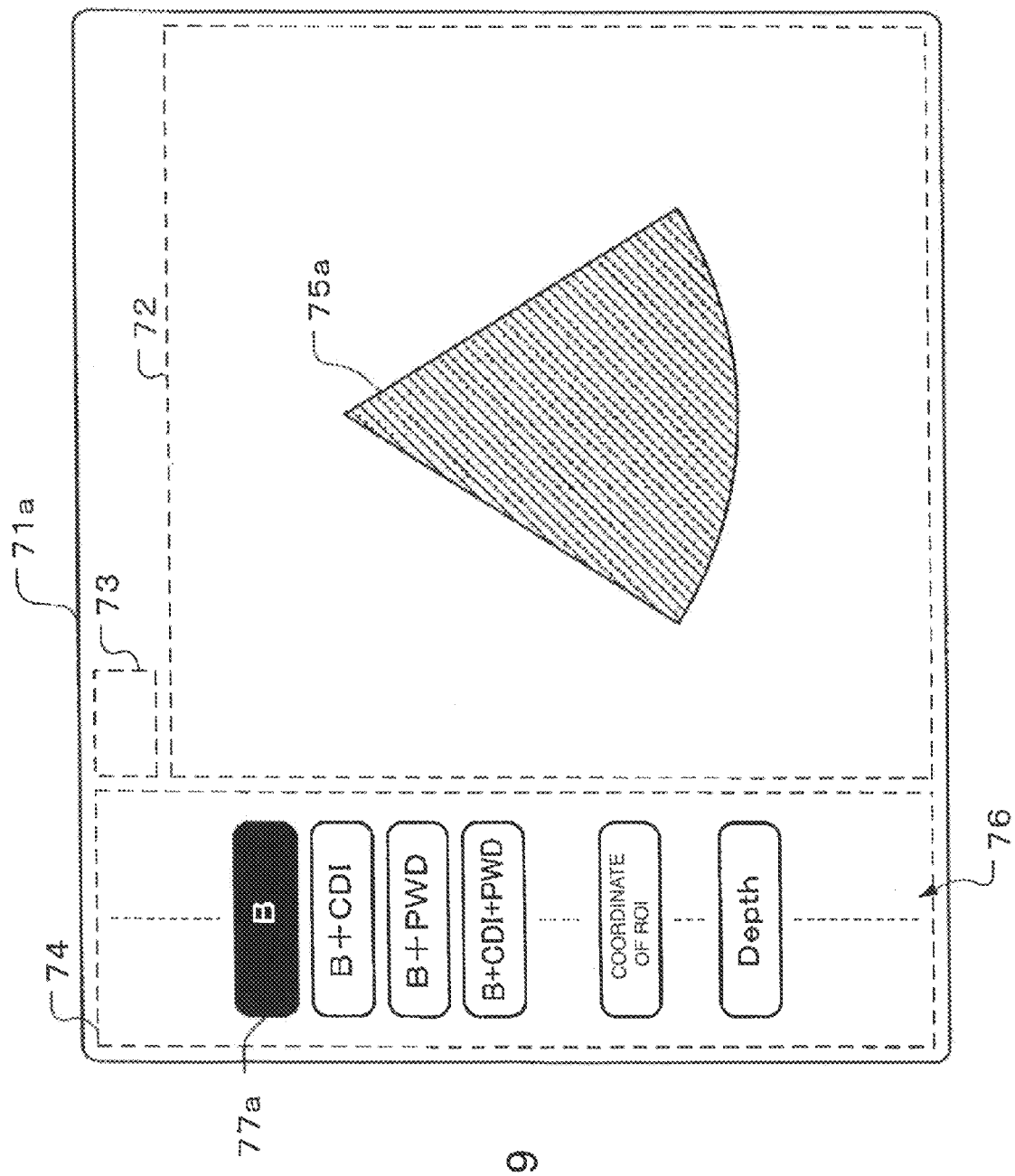
FIG. 9 illustrates an embodiment of B mode image data and an operation menu that are displayed on a display unit in the ultrasound diagnosis apparatus in accordance with analysis of movement of an ultrasound probe.

FIG. 9 illustrates embodiments of the B mode image data and the operation menu displayed on a screen in the display unit 7. In the first display area 72 of the display screen 71*a*, the B mode image data 75*a* is displayed in real time. In the third display area 74, the operation menu 76 including a plurality of operation keys "B", "B+CDI", "B+PWD", "B+CDI+PWD", "the coordinate of ROI" and "Depth", are displayed.

The operation key "B" corresponds to the generation mode for generating B mode image data. The operation key "B+CDI" corresponds to the generation mode for generating (B+CDI) image data. The operation key "B+PWD" corresponds to the generation mode for generating (B+PWD) image data. The operation key "B+CDI+PWD" corresponds to the generation mode for generating (B+CDI+PWD) image data. In this embodiment of the display, the cursor 77 is now identified on the operation key "B" displayed on the first display area 72 for generating B mode image data.

The operation key "coordinate of ROI" is used for setting the coordinate of ROI of the (B+CDI) image data displayed on the first display area 72. The operation key "Depth" is used for setting a viewing depth of B mode image data.

According to an embodiment consistent with the present invention, in accordance with the first moving operation of the ultrasound probe, the moving direction of the ultrasound probe can be acquired. By converting the acquired moving direction data to the first operation data, it becomes possible to display the operation menu 76 on the third display area 74 in the screen 71*a*. Accordingly, while both hands of an operator are occupied, it is easy to perform such input operations by simply stopping or wiggling the ultrasound probe similar to operations performed through the operation unit 8.

The second moving operation of the ultrasound probe can be performed to change the image data generation mode. In accordance with the second moving operation of the ultrasound probe, the operation converting unit 9 converts the moving direction data and the moving distance data output from the moving detection unit 52 to the second operation data for moving the cursor 77 in the operation menu 76 displayed at the third area 74 in the screen 71*a* shown in FIG. 9 in one direction. The converted data is output to the system control unit 10. In accordance with the second operation data output from the operation converting unit 9, the system control unit 10 moves the cursor 77 displayed in the third area 74 in the screen 71a onto, for example, the operation key "B+CDI".

Thus, the moving direction and the moving distance are acquired in accordance the second moving operation of the ultrasound probe. By converting the acquired moving direction data and the moving distance data to the second operation data, it becomes possible to move the cursor 77 displayed in the third area 74 in the screen 71a. Accordingly, even while both hands of an operator are occupied, the operator can easily perform a same input operation as input from the operation unit 8 by simply operating the ultrasound probe 1.

When the third moving operation of the ultrasound probe 1 is performed, the operation converting unit 9 can convert the moving direction data output from the moving detection unit 52 in accordance with the third moving operation to the third operation data for generating image data of the generation mode corresponded to the operation key "B+CDI" at the cursor position moved in the operation menu 76 displayed in the third display area 74 of the screen 71a. The converted third operation data is output to the system control unit 10. The system control unit 10 controls each of units in the apparatus based on the third operation data from the operation converting unit 9.

The color Doppler data generating unit 33 in the data generating unit 3 generates color Doppler data and stores it in the data memory unit 41. The image data generating unit 42 generates color Doppler image (CDI) data by reading out the color Doppler data stored in the data memory unit 41. By piling up the generated CDI data on a region of interest (ROI) of the generated B mode image data, the (B+CDI) image data is output to the display unit 7. The display unit 7 displays the (B+CDI) image data output from the image data generating unit 42 and the operation menu in which the cursor 77 is moved onto the operation key "B+CDI" (FIG. 7, step S4).

Figure 10:
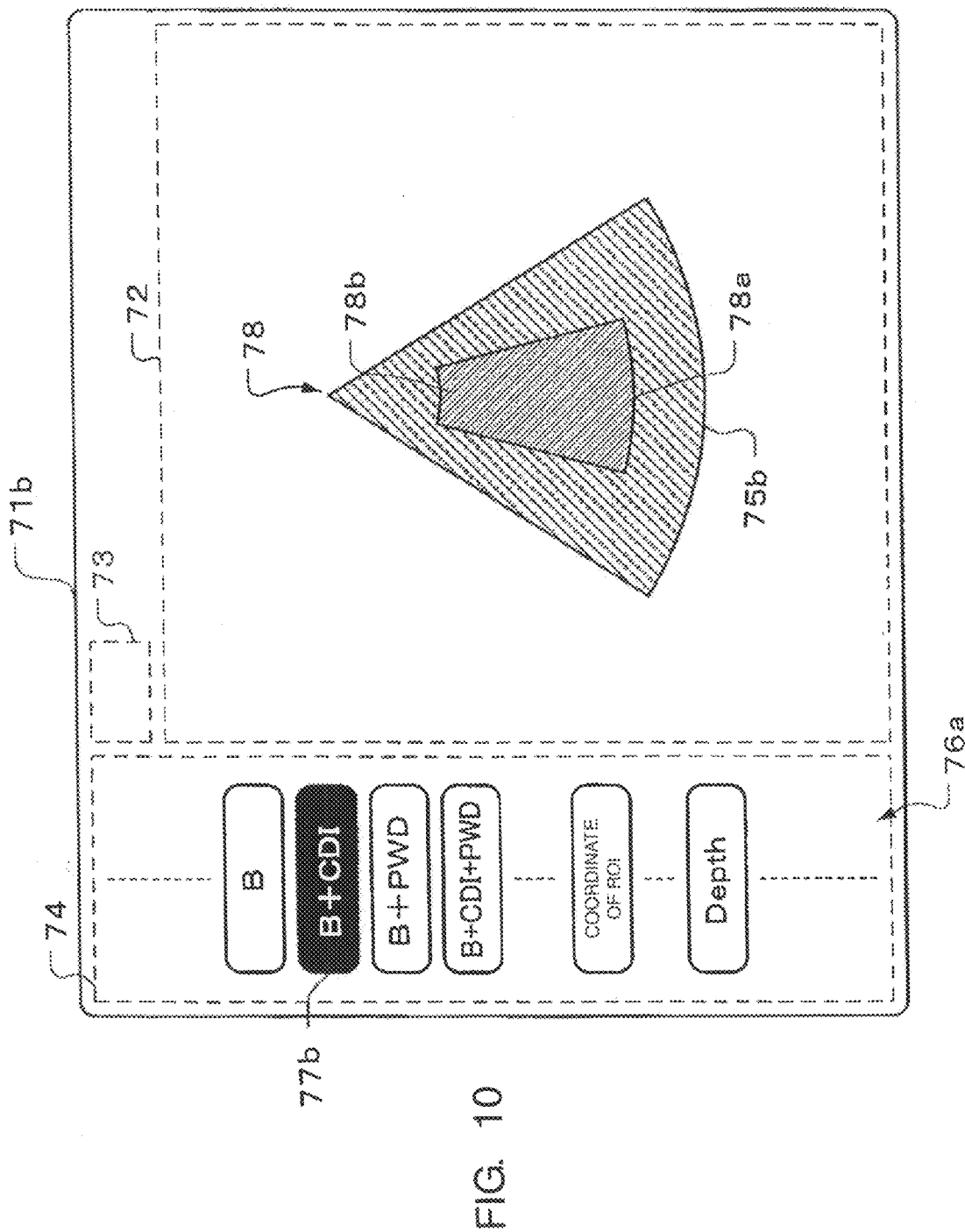
FIG. 10 illustrates an embodiment of B mode image data plus color Doppler image data and an operation menu that are displayed on a display unit in the ultrasound diagnosis apparatus in accordance with analysis of movement of an ultrasound probe.

FIG. 10 illustrates an example display of (B+CDI) image data and an operation menu displayed on a screen of the display unit 7. In the first display area 72 in the displayed screen 71b, (B+CDI) image data 78 is displayed in real time. (B+CDI) image data 78 displayed in the first display area 72 includes B mode image data 75b and CDI image data 78b piled up on the ROI 78a or ROI 78a in the B mode image data 75b.

In the third display area 74, the operation menu 76a is displayed. In this operation menu 76a, the cursor 77 is identified on the position "B+CDI" that is different from the operation menu 76 shown in FIG. 9.

In accordance with the third moving operation of the ultrasound probe, the moving direction is acquired. The acquired moving direction data can be converted to the third operation data for generating image data under the generation mode "B+CDI" corresponded to the position of the cursor 77 in the operation menu 76a displayed in the third display area 74 of the screen 71b. Thus, (B+CDI) image data 78 can be displayed in the first display area 72 of the screen 71b. Accordingly, even while both hands of an operator are occupied, the operator can easily perform the same input operation as input from the operation unit 8 by simply operating the ultrasound probe 1.

The second moving operation of the ultrasound probe is performed to change the coordinate of the ROI 78a displayed in the first display area 72 of the screen 71b. In accordance with the second moving operation, the operation converting unit 9 converts the moving direction data and the moving distance data output from the moving detection unit 52 to the second operation data for moving the cursor 77 in the operation menu 76a in one direction. Based on the second operation data output from the operation converting unit 9, the system control unit 10 moves the cursor 77 in the operation menu 76a displayed in the third display area 4 of the screen 71b to the position of "coordinate of ROI".

When the third moving operation of the ultrasound probe 1 is performed, the operation converting unit 9 can convert the moving direction data output from the moving detection unit 52 in accordance with the third moving operation to the third operation data that can change setting of the coordinate of ROI 78a displayed in the first display area 72 of the screen 71b corresponded to the moved position "coordinate of ROI" of the cursor 77 in the operation menu 6a displayed in the third display area 4 of the screen 71b. Based on the converted the third operation data, the system control unit 10 changes a setting of the coordinate of ROI 78a displayed in the first display area 72 of the screen 71b.

When the fourth or the fifth moving operation of the ultrasound probe 1 is performed, the operation converting unit 9 can convert the moving direction data and the moving distance data output from the moving detection unit 52 to the fourth or the fifth operation data in accordance with its moving operation. Based on the fourth or the fifth operation data output from the operation converting unit 9, the system control unit 10 performs a change setting of the coordinate of the ROI 78a displayed in the first display area 72 of the screen 71b. The system control unit 10 also displays the CDI image data of the set ROI.

By doing this, a moving direction and a moving distance are acquired in accordance with the fourth or the fifth moving operation of the ultrasound probe 1. By converting the acquired moving direction data and the moving distance data to the fourth or the fifth operation data, it can set a change of the coordinate for ROI 178a displayed on the screen 71B. It is also possible to display CDI image data of the set ROI. Consequently, even while both hands of an operator occupied, the operator can easily perform similar input operations as through the input operation unit 8 by operating the ultrasound probe 1 held in one hand.

When a stop of the examination for an object P is input from the operation unit 8, the system control unit 10 stops the operations of the transmission/reception unit 2, the data generating unit 3, the image data processing unit 4, the image data analyzing unit 5 and the display unit 7. Thus, the ultrasound diagnosis apparatus 100 ends the examination (FIG. 7, step S5).

According to the embodiments consistent with the present invention, in accordance with the operations of the ultrasound probe 1, an ultrasound diagnosis apparatus can acquire the movement data of the ultrasound probe 1 by analyzing two neighboring B mode image data generated in time series by the image data generating unit 42 or two neighboring B mode image data thinned out under a prescribed thin out interval. By converting the acquired movement data into the predetermined operation data, it can similarly perform the same input operation that is input from the operation unit 8.

According to the embodiments consistent with the present invention, an ultrasound diagnosis apparatus can display the stop time of the ultrasound probe 1 in real time at the second display area 73 in the screen 71 in accordance with the stop operation of the ultrasound probe. Further, in accordance with the storing operation of the ultrasound probe, it can store the image data generated by the image data generating unit 42 to the image data memory unit 6.

According to the embodiments consistent with the present invention, an ultrasound diagnosis apparatus can display the operation menu 76 in the third display area 74 of the screen 71a in accordance with the first moving operation. Further, in accordance with the second moving operation, it can move the cursor 77 in the operation menu 76 displayed at the third display area 74 in the display screen 71*a*.

According to the embodiments consistent with the present invention, in accordance with the third moving operation at the first display area 72 in the screen 71B, an ultrasound diagnosis apparatus can display the (B+CDI) image data 78 corresponding generation mode to the moved position (B+CDI) of the cursor 77 in the operation menu 76 displayed in the third display area 74 of the screen 71*a*. Further, an ultrasound diagnosis apparatus can change the setting of the coordinate of the ROI 178*a* displayed at the first display area 72 of the screen 71B and the CDI image data of the set ROI in accordance with the fourth or the fifth moving operation.

According to the embodiments consistent with the present invention, while both hands of an operator are occupied for another operation, it becomes possible to perform predetermined input operations through the operation of the ultrasound probe without confusing an object. Thus, an operator of an ultrasound probe can perform predetermined input operations during an operation for an examination without using an operation table or a remote controller. Consequently, it becomes possible to effectively perform an ultrasound diagnosis examination.

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

What is claimed is:

1. An ultrasound diagnosis apparatus comprising:
    an ultrasound probe including a plurality of transducers to emit ultrasounds based on driving signals and to receive ultrasounds reflected from objects;
    a transmission/reception unit to supply driving signals to a prescribed number of transducers and to obtain receiving signals based on the reflected ultrasounds;
    an image data generating unit to generate B mode image data by processing the receiving signals supplied from the transmission/reception unit;
    an image data analyzing unit to analyze at least one predetermined area of the B mode image data generated by the image data generating unit and to acquire movement data of the ultrasound probe;
    an operation conversion unit configured to convert the movement data of the ultrasound probe acquired from the image data analyzing unit to predetermined operation data; and
    a display unit configured to receive the operation data from the operation conversion unit and to display the B mode image data, wherein a display image screen on the display unit is changed based on the received operation data.

2. The ultrasound diagnosis apparatus according to claim 1, further comprising an operation unit to input data for performing examination of an object.

3. The ultrasound diagnosis apparatus according to claim 1, wherein in the display image screen on the display unit an operation menu is changed from a non-display status to a display status.

4. The ultrasound diagnosis apparatus according to claim 1, wherein the image data analyzing unit analyzes at least one predetermined area in each of two neighboring B mode image data generated at a time series, or at least one predetermined area in each of two neighboring B mode image data generated at a time series and thinned out at a prescribed thin out interval ratio, or at least one predetermined area at each of adjacent view corners of the generated B mode image data for acquiring the movement data of the ultrasound probe.

5. The ultrasound diagnosis apparatus according to claim 4, wherein the image data analyzing unit acquires a stop data of the ultrasound probe in contact with the object as one of the movement data based on a brightness value of the pixels in a whole area of the B mode image data when both of the neighboring B mode image data include pixels greater than an imaging threshold amount.

6. The ultrasound diagnosis apparatus according to claim 4, wherein the image data analyzing unit acquires lateral movement data for moving the ultrasound probe in contact with a body surface of the object based on a change of a brightness value at the at least one predetermined area provided at adjacent corners of the B mode image data, when both of the neighboring B mode image data include pixels greater than the imaging threshold.

7. The ultrasound diagnosis apparatus according to claim 6, wherein the image data analyzing unit acquires a parallel moving direction of a scan surface formed through the ultrasound scans by the transmission/reception unit moving along a body surface of the object and a parallel moving distance when all of moving directions of the ultrasound probe are in a same direction.

8. The ultrasound diagnosis apparatus according to claim 6, wherein the image data analyzing unit acquires pressurization/depressurization movement data of the ultrasound probe moving parallel to a scan surface, formed through ultrasound scans by a transmission/reception unit when all of moving directions of the ultrasound probe are in a same direction.

9. The ultrasound diagnosis apparatus according to claim 8, wherein the operation conversion unit converts the movement data acquired by the image data analyzing unit to the predetermined operation data in accordance with a plurality of reciprocating operations in a prescribed time period that move the ultrasound probe in one of the air direction or the contacting direction and then moves the ultrasound probe in the other direction.

10. The ultrasound diagnosis apparatus according to claim 8, wherein the operation conversion unit converts the movement data and the lateral movement data acquired by the image data analyzing unit to the predetermined operation data to the operation unit in accordance with a movement of the ultrasound probe that exceeds the prescribed scope in either of right or left directions after repeating the reciprocating movement in the prescribed scope during a predetermined time period.

11. The ultrasound diagnosis apparatus according to claim 10, further comprising:
    wherein the operation conversion unit converts the stop data of the ultrasound probe acquired by the image data analyzing unit to time operation data; and
    the display unit displays a stop time of the ultrasound probe calculated based on the converted time operation data with the B mode image data generated by the image data generating unit.

12. The ultrasound diagnosis apparatus according to claim 10, further comprising:
    an image data memory unit configured to store image data generated from the image data generating unit; and
    wherein the operation conversion unit converts the stop data acquired by the image data analyzing unit in accordance with the stop of the ultrasound probe during a prescribed time period to store operation data generated by the image data generating unit during the prescribed stop time period of the ultrasound probe into the image data memory unit.

13. The ultrasound diagnosis apparatus according to claim 4, wherein the image data analyzing unit acquires upward movement data of the ultrasound probe for moving from a contacting position on the object to an air position separated from the object, or vice versa a downward movement data of the ultrasound probe, when the at least one predetermined area of the one image data in the neighboring B mode image data includes pixels less than an imaging threshold and the at least one predetermined area of the other image data in the neighboring B mode image data includes pixels greater than an imaging threshold.

14. The ultrasound diagnosis apparatus according to claim 13, wherein the operation conversion unit converts the movement data acquired by the image data analyzing unit to the predetermined operation data in accordance with a plurality of reciprocating operations in a prescribed time period that move the ultrasound probe in one of the air direction or the contacting direction and then moves the ultrasound probe in the other direction.

15. The ultrasound diagnosis apparatus according to claim 13, wherein in the display image screen on the display unit a position of a cursor displayed in the operation menu is changed.

16. An ultrasound diagnosis apparatus comprising:
an ultrasound probe including a plurality of transducers to emit ultrasounds based on driving signals and receive ultrasounds reflected from objects;
a transmission/reception unit to supply driving signals to a prescribed number of transducers and to obtain receiving signals based on the reflected ultrasounds;
an image data generating unit to generate B mode image data by processing the receiving signals supplied from the transmission/reception unit;
means for analyzing unit at least one predetermined area of the B mode image data generated by the image data generating unit and to acquire movement data of the ultrasound probe;
means for converting the movement data of the ultrasound probe to a predetermined operation data; and
means for receiving the operation data, and for displaying the B mode image data such that a display image screen is changed based on the received operation data.

* * * * *